US008118022B2

(12) United States Patent
Chambers

(10) Patent No.: US 8,118,022 B2
(45) Date of Patent: Feb. 21, 2012

(54) SELF-CONTAINED BREATHING APPARATUS (SCBA) WITH SAFETY QUICK DISCONNECT FOR PERMITTING SAFE AND READY ACCESS TO A REPLACEMENT BREATHING COMPONENT

(75) Inventor: Paul A. Chambers, Harvard, MA (US)

(73) Assignee: Avon Protection Systems, Inc., Cadillac, MI (US)

( * ) Notice: Subject to any disclaimer, the term of this patent is extended or adjusted under 35 U.S.C. 154(b) by 1078 days.

(21) Appl. No.: 12/006,667

(22) Filed: Jan. 3, 2008

(65) Prior Publication Data

US 2008/0178878 A1 Jul. 31, 2008

Related U.S. Application Data

(60) Provisional application No. 60/878,338, filed on Jan. 3, 2007, provisional application No. 60/925,314, filed on Apr. 19, 2007, provisional application No. 60/965,464, filed on Aug. 20, 2007.

(51) Int. Cl.
*A61M 11/00* (2006.01)

(52) U.S. Cl. .............................. 128/202.27; 128/205.28

(58) Field of Classification Search ............. 128/202.26, 128/202.27, 205.12, 205.28, 205.17
See application file for complete search history.

(56) References Cited

U.S. PATENT DOCUMENTS

| | | | | |
|---|---|---|---|---|
| 2,948,553 | A | 8/1960 | Gill et al. | |
| 3,077,880 | A | 2/1963 | Morton, Jr. | |
| 4,168,706 | A * | 9/1979 | Fletcher et al. | 128/204.16 |
| 4,300,547 | A * | 11/1981 | Pasternack | 128/202.26 |
| 4,342,913 | A | 8/1982 | Shepherd | |
| 4,409,978 | A * | 10/1983 | Bartos | 128/205.12 |
| 4,794,923 | A * | 1/1989 | Bartos | 128/205.24 |
| 4,821,711 | A * | 4/1989 | Eckstein et al. | 128/202.26 |
| 5,619,988 | A | 4/1997 | Mattila et al. | |
| 5,746,199 | A | 5/1998 | Bayron et al. | |
| 6,761,162 | B1 | 7/2004 | Swann | |
| 2002/0135488 | A1 | 9/2002 | Hibbs et al. | |
| 2002/0155622 | A1 | 10/2002 | Slater et al. | |
| 2003/0188744 | A1 | 10/2003 | Deas et al. | |
| 2006/0076896 | A1 | 4/2006 | Osborn et al. | |
| 2006/0175565 | A1 | 8/2006 | Nungesser et al. | |
| 2006/0201509 | A1 * | 9/2006 | Forsyth et al. | 128/204.26 |
| 2007/0060874 | A1 | 3/2007 | Nesbitt et al. | |

OTHER PUBLICATIONS

Ocenco, Inc. EBA 6.5 product brochure, Dec. 3, 2003, http://web.archive.org/web/20031203154508/http://ocenco.com/EBA6.5.pdf.
Kyriazi et al., "Self-Contained Self-Rescuer Field Evaluation: Seventh Phase Results", Mar. 2002.

* cited by examiner

*Primary Examiner* — Steven Douglas
(74) *Attorney, Agent, or Firm* — Pandiscio & Pandiscio

(57) ABSTRACT

A self-contained breathing apparatus (SCBA) comprising: a mouthpiece; a breathing component; and a safety quick disconnect comprising: a valve body; a valve spool comprising an L-shaped channel formed such that when the valve spool is appropriately rotated, the L-shaped channel (i) places an opening of the valve body in communication with a first port, or (ii) places the opening in communication with a second port; and a lock mechanism for (i) preventing the valve spool from rotating unless the breathing component is positioned in one of first and second mounts formed on the valve body adjacent the first and second ports, and a replacement breathing component is positioned in the other of the first and second mounts, and (ii) preventing the removal of a breathing component from a mount adjacent to a port which is in communication with the opening.

16 Claims, 16 Drawing Sheets

ONLY SIDE SWITCHED TO IS ACTIVE

TWO ELEMENTS CONNECTED

SELF-CONTAINED BREATHING APPARATUS (SCBA) WITH SAFETY QUICK DISCONNECT FOR PERMITTING SAFE AND READY ACCESS TO A REPLACEMENT BREATHING COMPONENT

REFERENCE TO PENDING PRIOR PATENT APPLICATIONS

This patent application claims benefit of:

(i) pending prior U.S. Provisional Patent Application Ser. No. 60/878,338, filed Jan. 3, 2007 by Paul A. Chambers for SELF CONTAINED SELF RESCUER-PLUS;

(ii) pending prior U.S. Provisional Patent Application Ser. No. 60/925,314, filed Apr. 19, 2007 by Paul A. Chambers for SELF CONTAINED SELF RESCUER-PLUS; and (iii) pending prior U.S. Provisional Patent Application Ser. No. 60/965,464, filed Aug. 20, 2007 by Paul A. Chambers for UNIVERSAL MINER SELF RESCUER (UMSR).

The three above-identified patent applications are hereby incorporated herein by reference.

FIELD OF THE INVENTION

This invention relates to self-contained breathing apparatuses (SCBAs) in general, and more particularly to a self-contained breathing apparatus with a safety quick disconnect for permitting safe and ready access to a replacement breathing component.

BACKGROUND OF THE INVENTION

The nature of underground mining operations makes them highly dangerous.

For example, in the case of a mine collapse, the supply of breathable air can be severely compromised, placing the miners in great danger.

Furthermore, mines are often highly susceptible to the infusion of noxious gases (e.g., methane, carbon monoxide, etc.). This situation can occur in many scenarios, even where there is no catastrophic mine collapse. Gas pockets can be exposed at any time and without notice, and can be life-threatening even where the mine is structurally intact. In any of these situations, once the gas enters the space occupied by the miners, their lives are in serious danger.

In all of these situations, the miners must quickly recognize the danger and then must obtain an supply of breathable air. This supply of breathable air may be provided by various means, e.g., a filtered system, a conventional "open-loop" self-contained breathing apparatus (SCBA), a conventional "closed-loop" self-contained breathing apparatus (SCBA), a solid state oxygen generator, etc. The equipment for providing the supply of breathable air is commonly referred to as a Self Rescuer and is generally carried by the miners on their belts. Once the miners have "switched over" to this supply of breathable air, they must then escape the danger zone. In the case of a "benign" gas pocket, escape may be as simple as walking or riding a mine car out of the affected area. In the case of a mine collapse, gas explosion, or other serious event, escape may involve crawling, tunneling, walking or just waiting for rescue. In any of these latter situations, there is a significant danger that the supply of breathable air may be depleted before the miner has reached a safe location.

At the same time, in many of these situations, it is not possible for the miners to use conventional negative pressure filtered respirators, powered air purifying respirator (PAPR), etc. due to the nature of the threat, e.g., the possible air contaminants (e.g., some gases), the physical state of the ambient air (e.g., super-heated air), etc. In these situations, a self-contained breathing apparatus (SCBA) is required.

Conventional "open-loop" SCBA units generally consist of a tank of compressed gas (usually ambient, but filtered, air) with the flow controlled by a regulator or demand valve. One of the major inefficiencies of these units is that the exhausted and/or exhaled air (still containing significant usable oxygen) is vented to the environment and thus lost to the user. Much greater efficiencies (translating into smaller, lighter units and longer supply times) can be attained by using "closed loop" SCBA units which recycle the exhaust air and recover the oxygen, and/or remove the undesirable products of respiration (mainly carbon dioxide). A device utilizing this approach is commonly referred as a "Rebreather". See FIG. 1.

Any respirator device, whether filtered, open-loop SCBA, closed-loop SCBA, etc. has a limited capacity to supply breathable air. If the miners exhaust the capacity of the respirator device while still in a dangerous environment, the miners must be able to access a replacement breathing component and make the "change-over" to the replacement breathing component without "breaking the seal" or otherwise exposing themselves to breathing in the potentially noxious gases.

As a result, a primary object of the present invention is to provide a self-contained breathing apparatus (SCBA) which is able to safely and quickly connect to a replacement breathing component without "breaking the seal" so that the replacement breathing component can supply additional breathing capacity to the user. Preferably, the replacement breathing component can take any number of forms, e.g., the working portion of another "closed-loop" SCBA, an air bottle, a carbon monoxide filter respirator, etc.

SUMMARY OF THE INVENTION

The present invention provides a self-contained breathing apparatus (SCBA) which is able to safely and quickly connect to a replacement breathing component without "breaking the seal" so that the replacement breathing component can supply additional breathing capacity to the user.

In one form of the present invention, there is provided a self-contained breathing apparatus (SCBA) comprising:

a mouthpiece;

a breathing component for providing breathable air, the breathing component comprising a component interface; and a safety quick disconnect comprising:

a valve body defining:

- an internal chamber;
- an opening communicating with the internal chamber and connectable with the mouthpiece;
- first and second ports communicating with the internal chamber;
- first and second mounts formed on the body adjacent to the first and second ports, respectively, for receiving the component interface of the breathing component, the first and second mounts being configured so as to place the breathing component into communication with the internal chamber when the component interface is in engagement with one or the other of the first and second mounts;

a valve spool selectively rotatably disposed within the internal chamber, wherein the valve spool comprises an L-shaped channel formed such that when the valve spool is appropriately rotated, the L-shaped channel (i) places the opening in communication with the first port, or (ii) places the opening in communication with the second port; and a lock mechanism for (i) preventing the valve spool from being rotated unless the component interface of the breathing component is positioned in one of the first and second mounts and a component interface of a replacement breathing component is positioned in the other of the first and second mounts, and (ii) preventing the removal of a component interface from a mount adjacent to a port which is in communication with the opening.

In another form of the present invention, there is provided a self-contained breathing apparatus (SCBA) comprising:

a mouthpiece;

a counterlung; and a breathing component interposed between the mouthpiece and the counterlung, the breathing component being adapted to provide breathable air; wherein the counterlung is sized so as to have a volume which is approximately equal to the tidal volume of a pair of adult lungs.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like elements and further wherein.

DETAILED DESCRIPTION OF THE INVENTION

Figure 1:
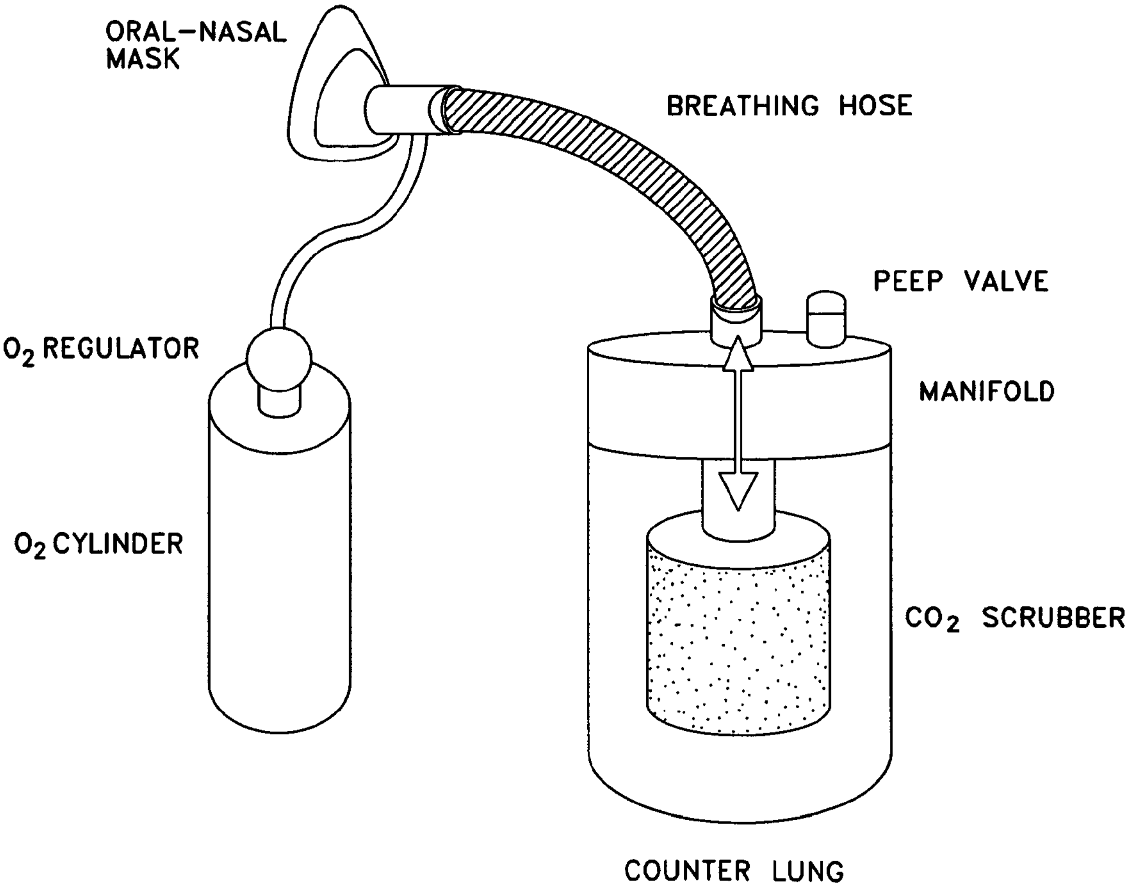
FIG. 1 (PRIOR ART)
FIG. 1 is a schematic view showing a prior art SCBA.
Figure 2:
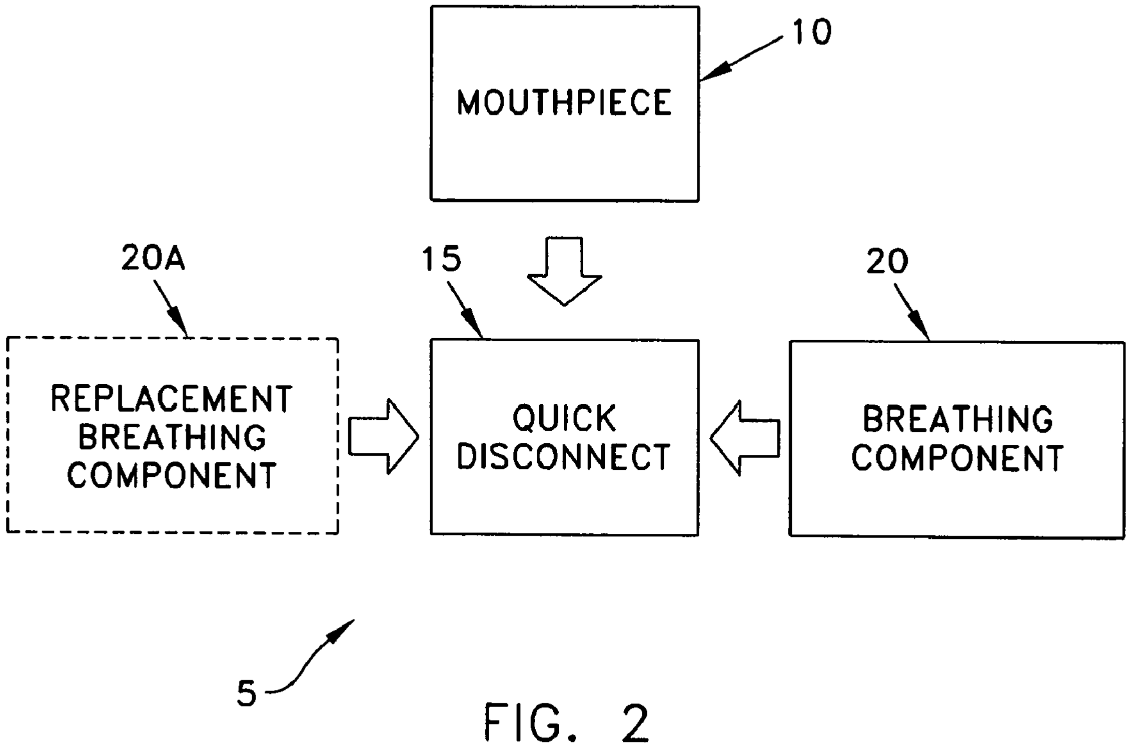
FIG. 2 is a schematic diagram showing a high-level overview of a novel SCBA formed in accordance with the present invention.
Figure 3:
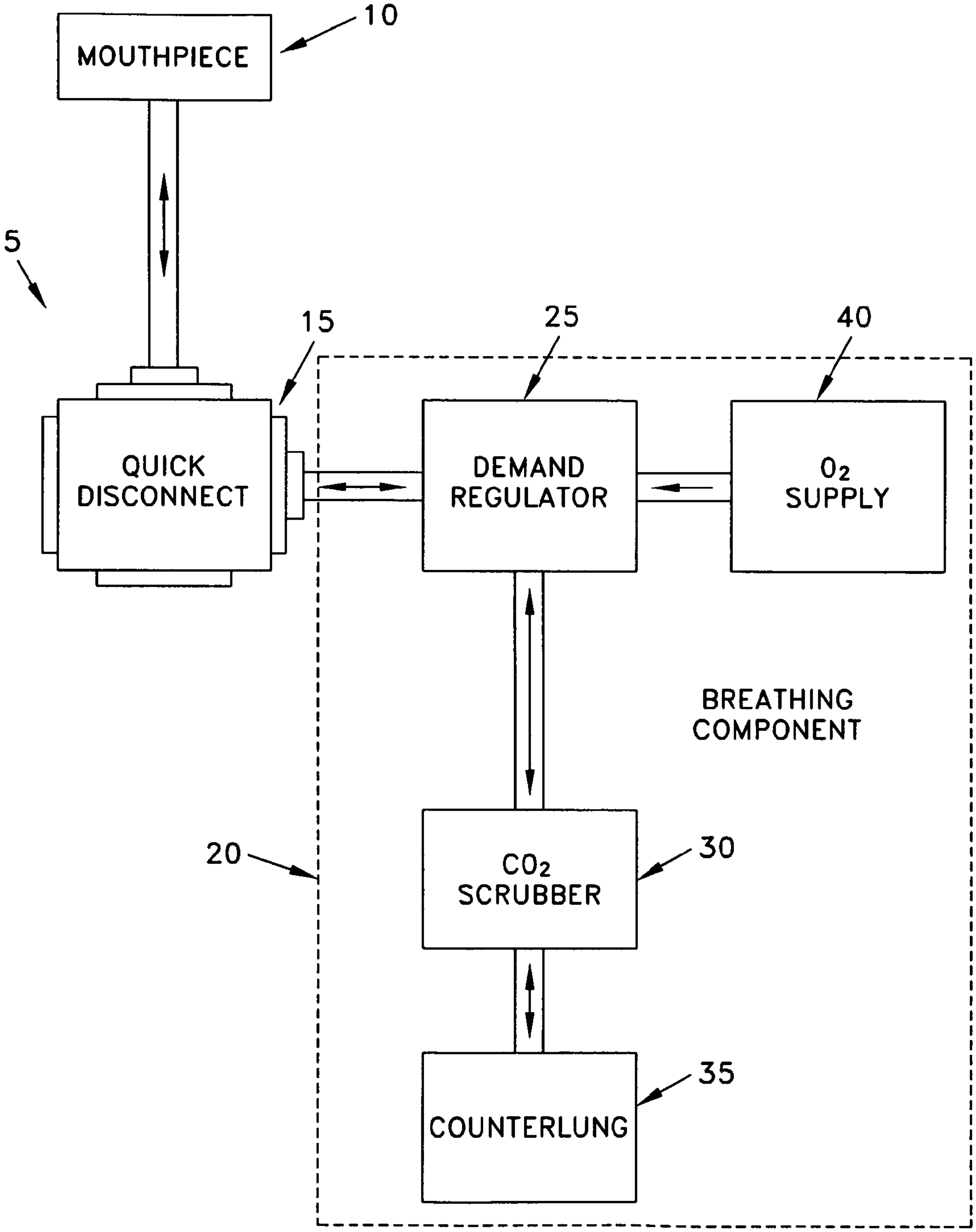
FIG. 3 is a schematic diagram showing a more detailed illustration of a novel SCBA formed in accordance with the present invention.

Looking next at FIGS. 2 and 3, there is shown a novel self-contained breathing apparatus (SCBA) 5 formed in accordance with the present invention. SCBA 5 generally comprises a mouthpiece 10 which is releasably connected to a multi-port safety quick disconnect 15. Also connected to quick disconnect 15 is a breathing component 20. A replacement breathing component 20A may also be connected to quick disconnect 15 when breathing component 20 is to be replaced.

Figure 4:
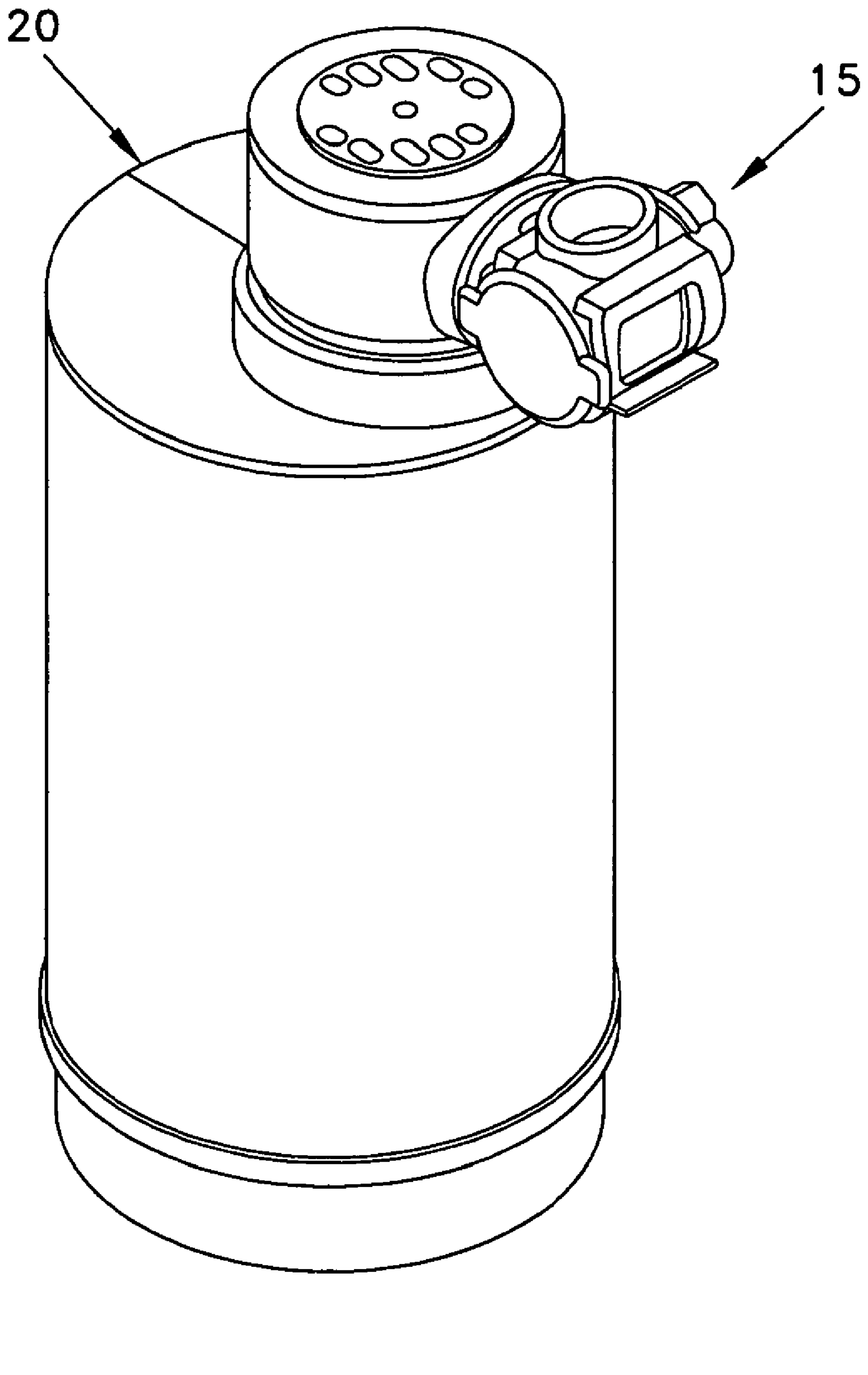
FIG. 4 is a schematic view showing a novel breathing component formed in accordance with the present invention.
Figure 5:
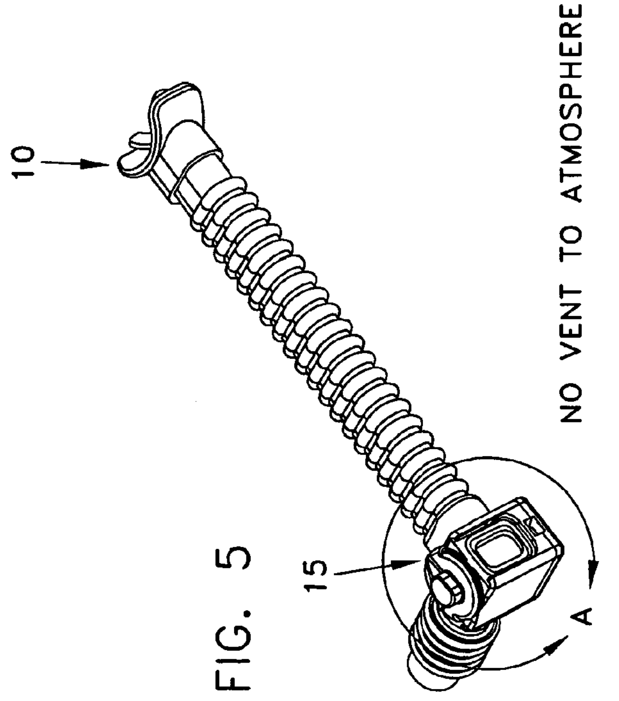
FIGS. 5-11 are schematic views showing a novel safety quick disconnect of the present invention.

Looking now at FIGS. 2-4, breathing component 20 preferably comprises a demand regulator 25, a carbon dioxide scrubber 30 and a counterlung 35. Breathing component 20 also comprises an oxygen supply 40.

During use, the user places mouthpiece 10 in their mouth and inhales and exhales through their mouth (a noseclip may also be supplied to restrict breathing through the nose and permit breathing through only the mouth). As air is exhaled, it passes through demand regulator 25, through carbon dioxide scrubber 30 and fills counterlung 35. As this occurs, carbon dioxide scrubber 30 purges carbon dioxide from the exhaled air. Conversely, as air is inhaled, air is drawn from counterlung 35, through carbon dioxide scrubber 30, through demand regulator 25 and back into the lungs of the user. Again, as the air from counterlung 35 passes through carbon dioxide scrubber 30, the scrubber purges carbon dioxide from the air.

Demand regulator 25 monitors the air pressure in the system and, when the air pressure falls below a certain threshold, releases supplemental oxygen from oxygen supply 40. More particularly, as the user breathes, the body metabolizes oxygen and releases carbon dioxide. This carbon dioxide is then removed from the system by carbon dioxide scrubber 30. Therefore, in a "closed-loop" system, as the user breathes, oxygen is consumed by the user, carbon dioxide is consumed by the scrubber, and the quantity of air is reduced. To that end, demand regulator 25 monitors the air pressure in the system and, as the quantity of air is reduced during breathing and scrubbing (which also reflects a reduction in the quantity of oxygen available for breathing), demand regulator 25 releases supplemental oxygen to the system to compensate for the consumed gases.

As a result of this construction, breathing component 20 is designed to provide extended breathing capacity, due to the use of (i) carbon dioxide scrubber 30, which allows the re-breathing of exhaled air, and (ii) demand regulator 25 and oxygen supply 40, which supply supplemental oxygen to the system as oxygen is consumed through breathing.

Significantly, counterlung 35 is carefully configured so as to have a size approximately equal to tidal volume of a pair of human lungs. This is approximately three times smaller than traditional counterlungs. By configuring counterlung 35 with this unique size, breathing component 20 ensures that demand regulator 25 will release fresh oxygen to the system before the oxygen content of the air being re-breathed falls to a level which is too low to safely sustain the user. More particularly, with each breath of the user, approximately 20% of the oxygen inhaled is consumed by the body and is replaced with exhaled carbon dioxide. This exhaled carbon dioxide is in turn purged by carbon dioxide scrubber 30. Thus, in the absence of a supplemental oxygen source, as the user breathes, the total quantity of air will continuously decrease as the carbon dioxide is pulled from the air. If counterlung 35 is made too large, it will take too long for the quantity of air in the system to be depleted to the point where demand regulator 25 will trigger the release of supplemental oxygen from oxygen supply 40. On the other hand, if counterlung 35 is formed too small, a user will not be able to inhale and exhale a full breath, which is important in emergency breathing situations where the user may need to be moving about rapidly. Sizing counterlung 35 so as to be the approximately the size of the tidal volume of a pair of lungs is a new and significant advance in the art.

Figure 6:
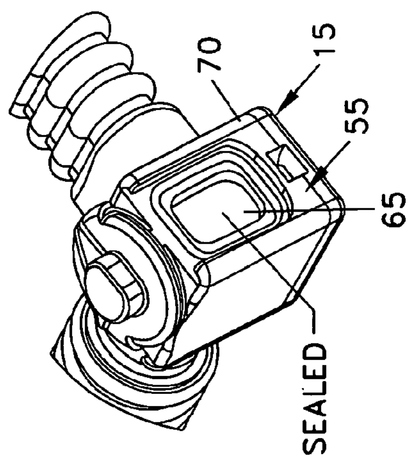
Figure 7:
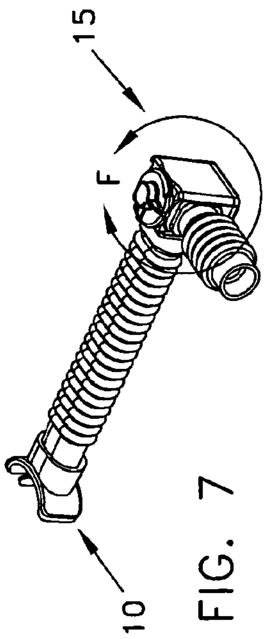
Figure 8:
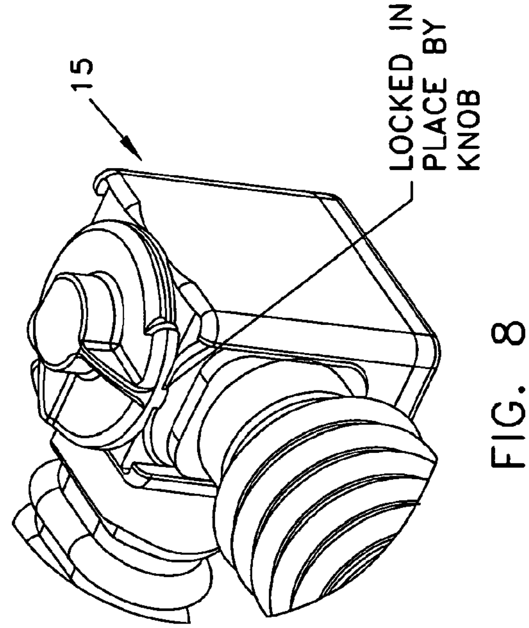
Figure 9:
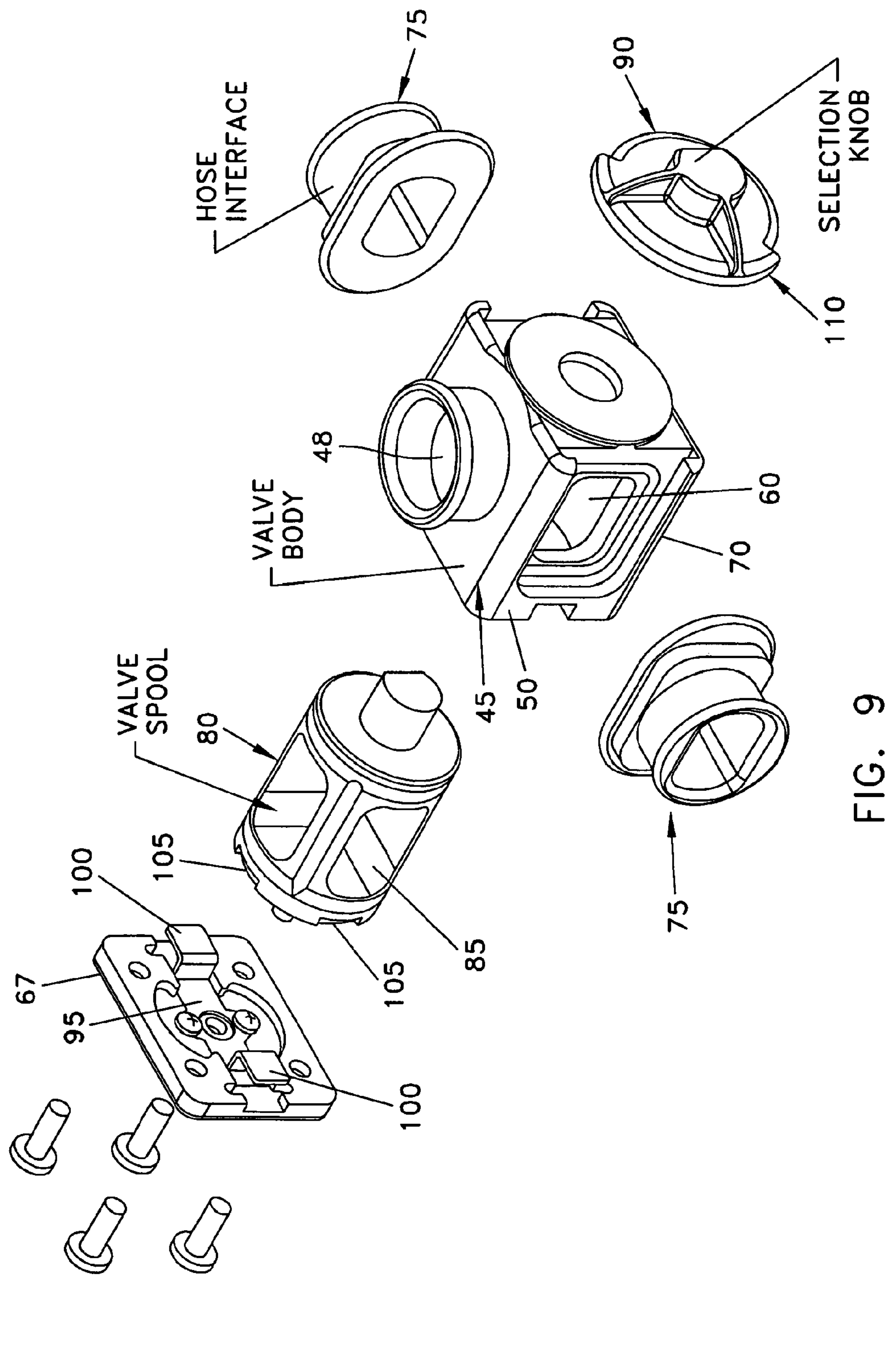
Figure 10:
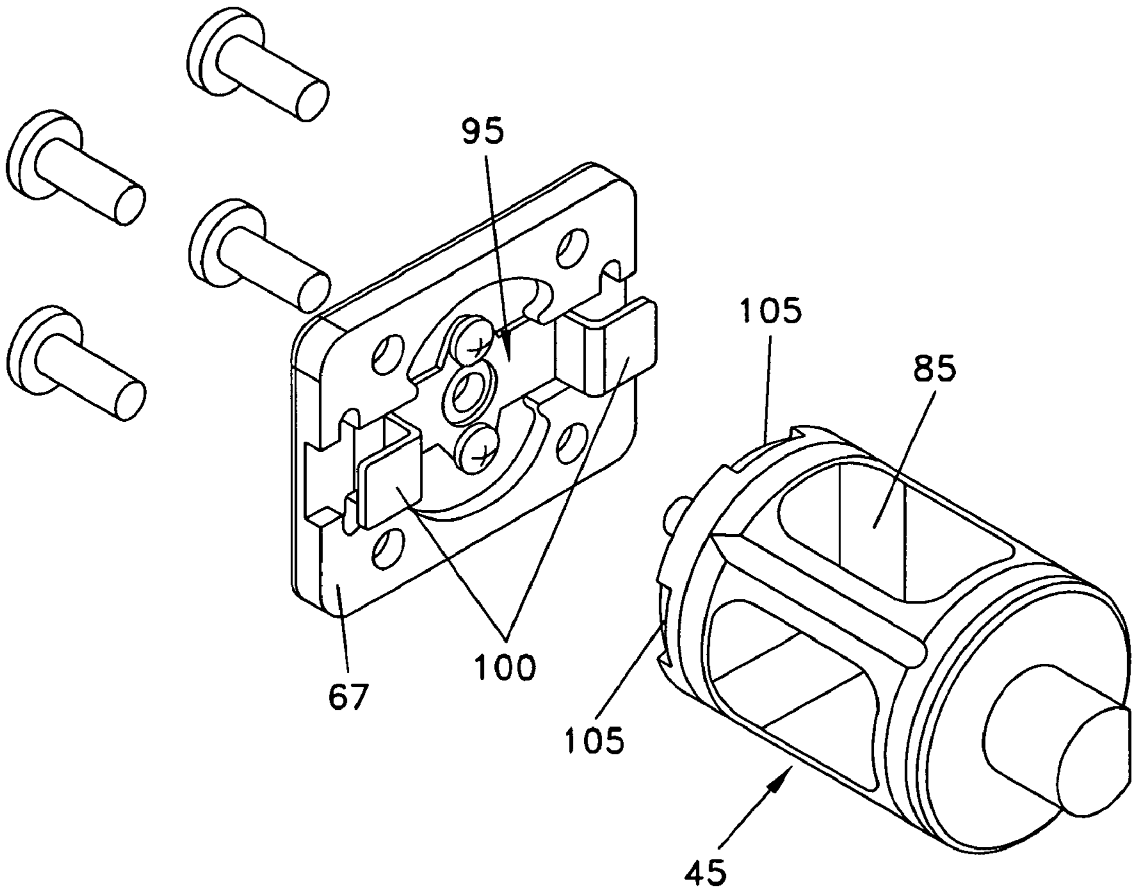
Figure 11:
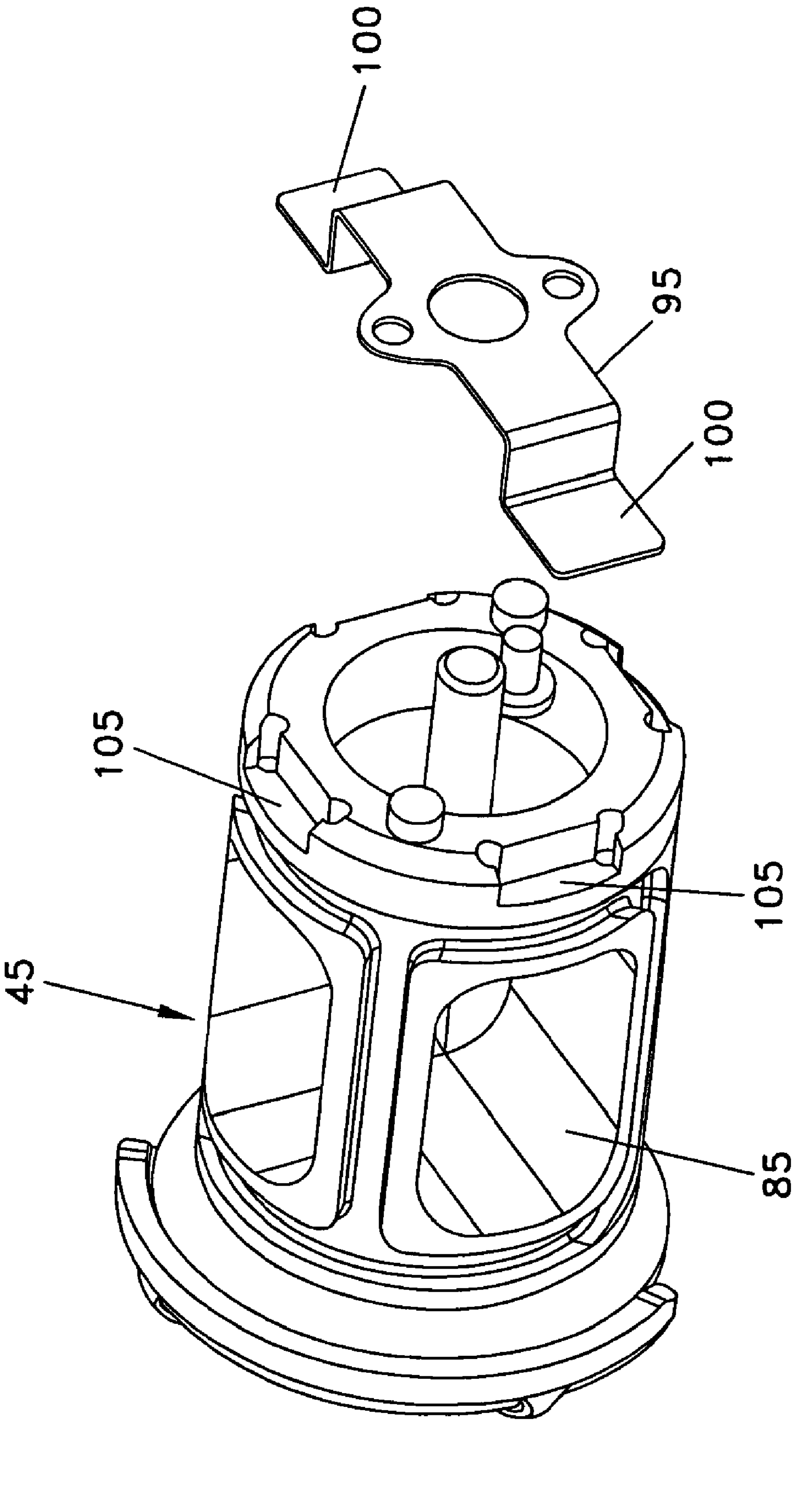

In another significant advance over the prior art, SCBA 5 utilizes a multi-port safety quick disconnect 15 to permit replacement breathing component 20A to be safely and quickly connected to mouthpiece 10 without "breaking the seal", so that additional breathing capacity can be safely supplied to the user when necessary. More particularly, any breathing component (e.g., a "closed-loop" SCBA system, a carbon dioxide absorber, an oxygen tank, etc.) has a finite functional lifetime: at the end of that functional lifetime, the breathing component must ultimately be replaced with a fresh unit in order to sustain a user. The present invention provides novel multi-port safety quick disconnect 15 to permit replacement breathing component 20A to be safely and quickly connected to mouthpiece 10 without "breaking the seal", so that additional breathing capacity can be safely supplied to the user when necessary Safety disconnect 15 is shown in greater detail in FIGS. 5-11. Safety disconnect 15 generally comprises a hollow rectangular valve body 45 having a top opening 48 for connecting to mouthpiece 10, two faces 50, 55 (FIGS. 6 and 9) with ports 60, 65 formed therein, respectively, and a back plate 67 for closing off valve body 45. The faces 50, 55 are each configured with a U-shaped rail 70 for slidably receiving, and forming an airtight seal with, a component interface 75 which connects with a breathing component. A cylindrical valve spool 80, with an L-shaped channel 85 formed therein, is rotatably disposed within valve body 45. A selection knob 90 is provided to permit the user to adjust the rotational position of valve spool 80 within valve body 45. As a result of this construction, L-shaped channel 85 can be used to connect port 60 with opening 48 or, alternatively, port 65 with opening 48.

Significantly, means are provided for restricting the position of valve spool 80 within valve body 45, and for restricting the inadvertent removal of a component interface 75 from valve body 45, whereby to present a user from accidentally breathing ambient air.

More particularly, back plate 67 includes a locking clip 95 having a pair of projecting spring fingers 100. Valve spool 80 includes four recesses 105 formed therein for selectively receiving spring fingers 100 of locking clip 95. As a result of this construction, valve spool 80 may not be rotated within valve body 45 unless, and until, two component interfaces 75 are pressed sufficiently rearwardly within U-shaped rail 70 as to push the two corresponding projecting spring fingers 100 out of their corresponding spool recesses 105.

Furthermore, selection knob 90 is provided with a peripheral extension 110 along a portion of its perimeter which prevents accidental removal of the component interface 75 selected by and in use on that corresponding side of the valve body so as to prevent the user accidentally disconnecting the active breathing air supply and exposing the corresponding port 60, 65 to atmosphere.

In addition to the foregoing, valve spool 80 is formed so that when it is in a locked position (i.e., so that a spring finger 100 is received in a spool recess 105), L-shaped channel 85 is connecting either port 60 with opening 48 or port 65 with opening 48.

Figure 12:
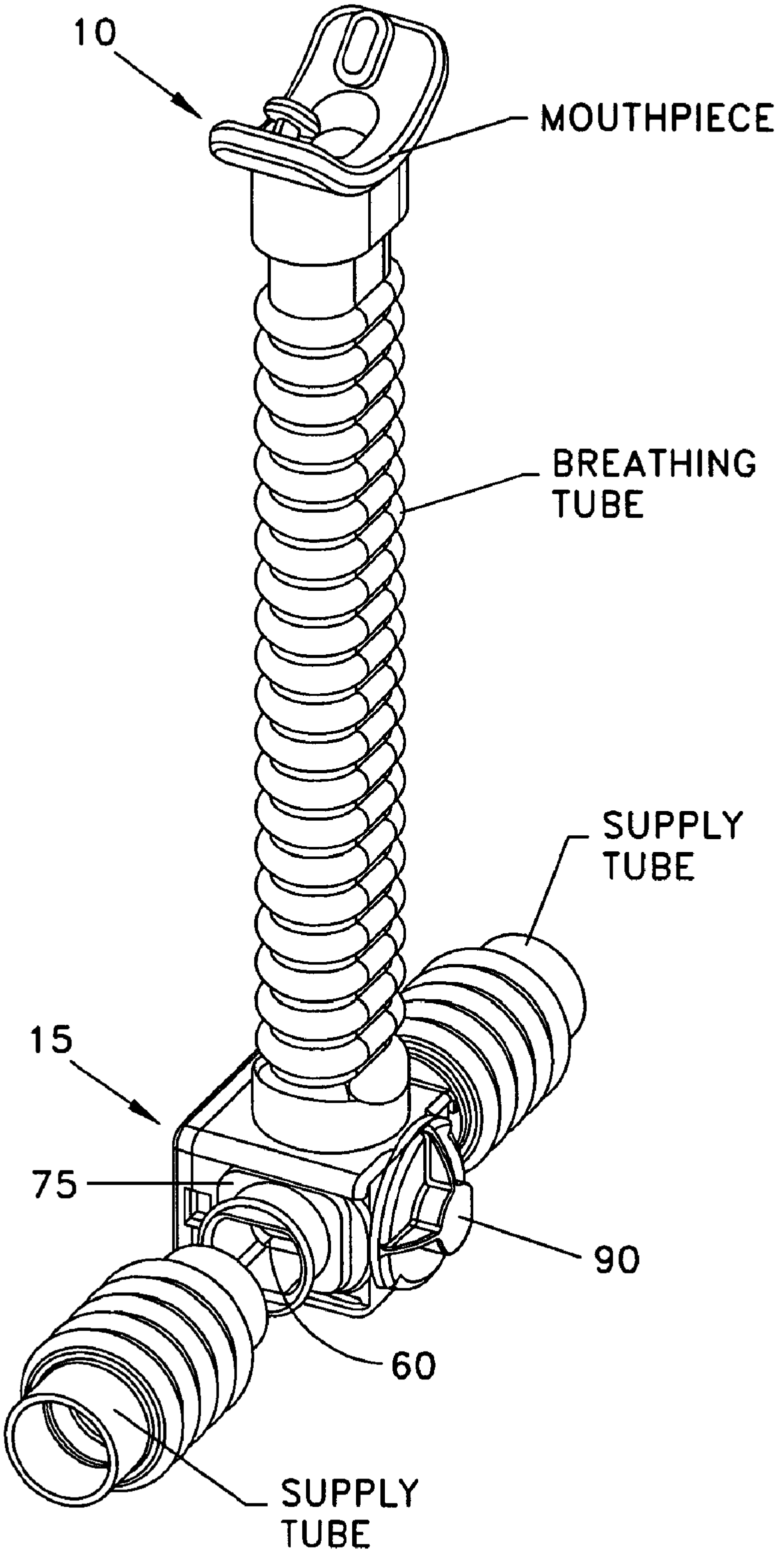
FIGS. 12-14 are schematic views illustrating how a breathing component and a replacement breathing component may be simultaneously connected to the safety quick disconnect, with only one breathing component being operable at a given time.
Figure 14:
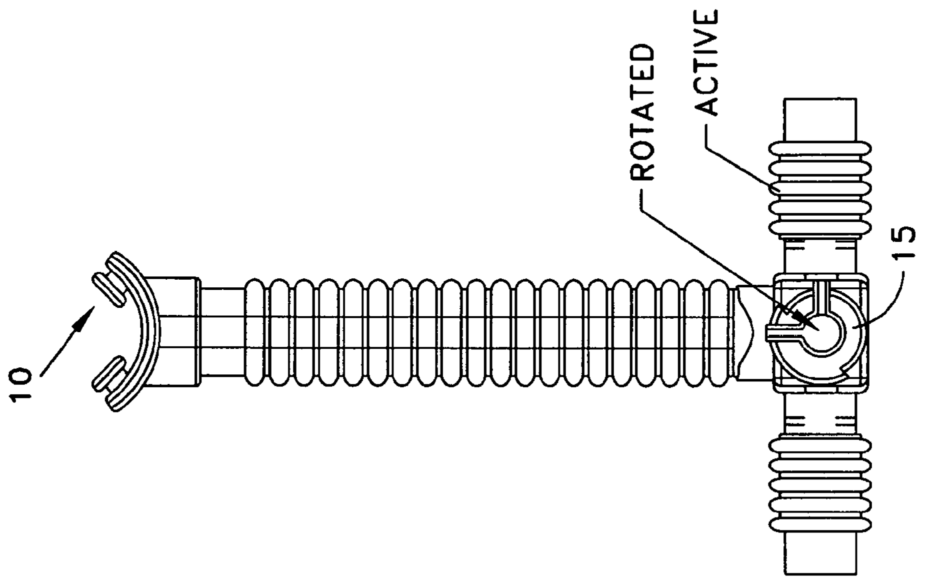
Figure 13:
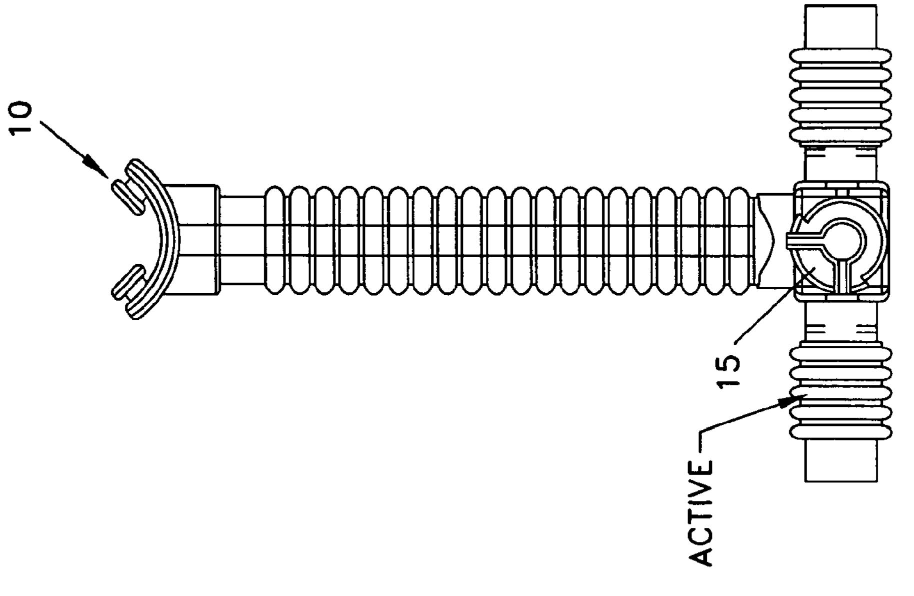
Figure 17:
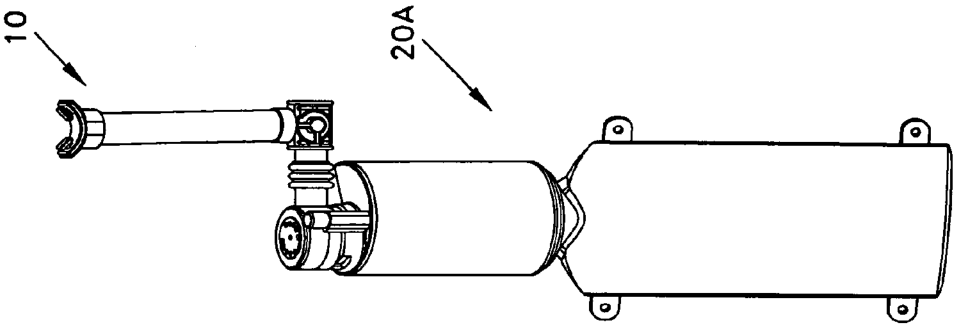
FIGS. 15-17 are schematic views showing how a depleted breathing component may be "switched out" (i.e., changed over) to a replacement breathing component.
Figure 16:
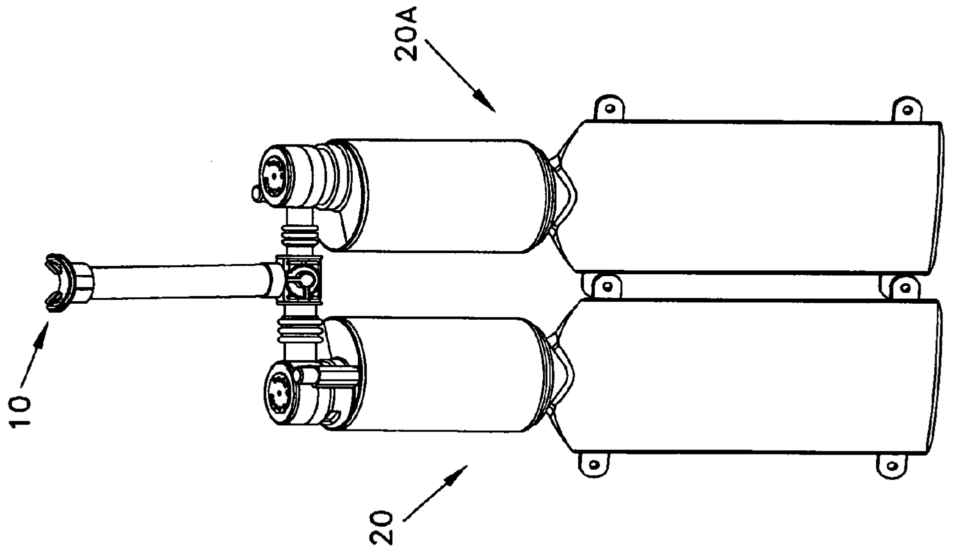
Figure 15:
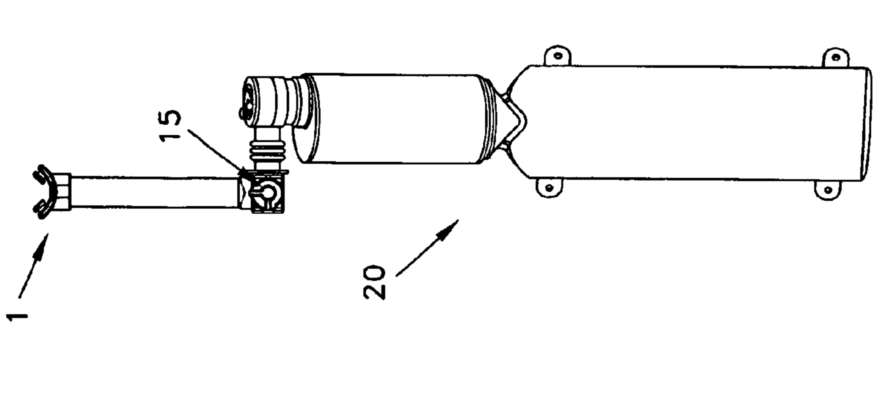
Figure 19:
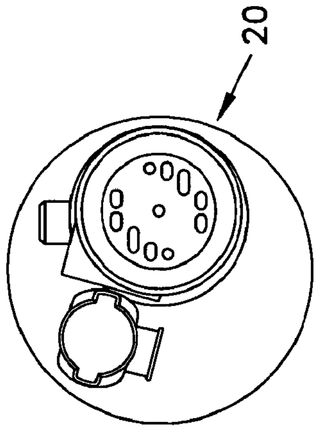
FIGS. 18-23 are schematic views illustrating various configurations for a novel breathing component formed in accordance with the present invention.
Figure 21:
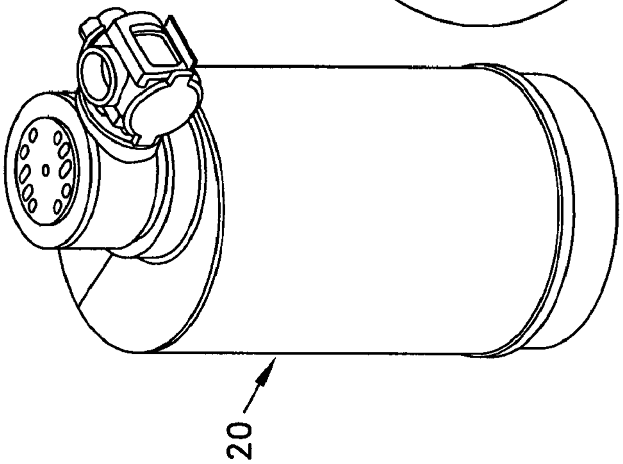
Figure 20:
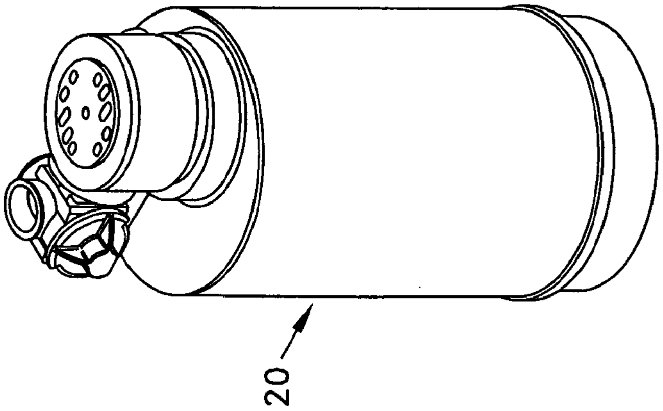
Figure 18:
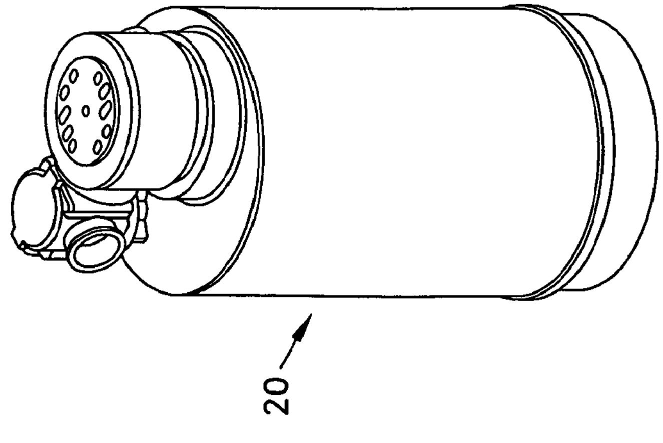

As a result of this construction, a component interface 75 may only be withdrawn when another component interface 75 has been connected to quick disconnect 15 and valve knob 90 has been rotated to select the side being retained as a breathing source. Furthermore, as shown in FIGS. 12-14, only one port 60, 65 may be open at any given time to mouthpiece 10. Thus, the mouthpiece can never be opened to ambient air. As a result, multi-port safety quick disconnect 15 permits a replacement breathing component to be safely and quickly connected to mouthpiece 10 without "breaking the seal", so that additional breathing capacity can be safely supplied to the user. In other words, a user cannot disconnect from a current breathing component unless, and until, a replacement breathing component has been properly connected to multi-port quick disconnect 15. Thus, the construction quick disconnect 15 prohibits a user from (i) accidentally disengaging a current breathing component until a replacement breathing component has been connected, and (ii) inadvertently connecting the mouthpiece to ambient air.

In other words, the foregoing construction permits a first breathing component is to be safely and readily replaced with a replacement breathing component when necessary. More particularly, and looking now at FIGS. 15-18, safety quick disconnect 15 permits a first breathing component 20 to be replaced with a replacement breathing component 20A, and the first breathing component 20 to be thereafter discarded.

Figure 22:
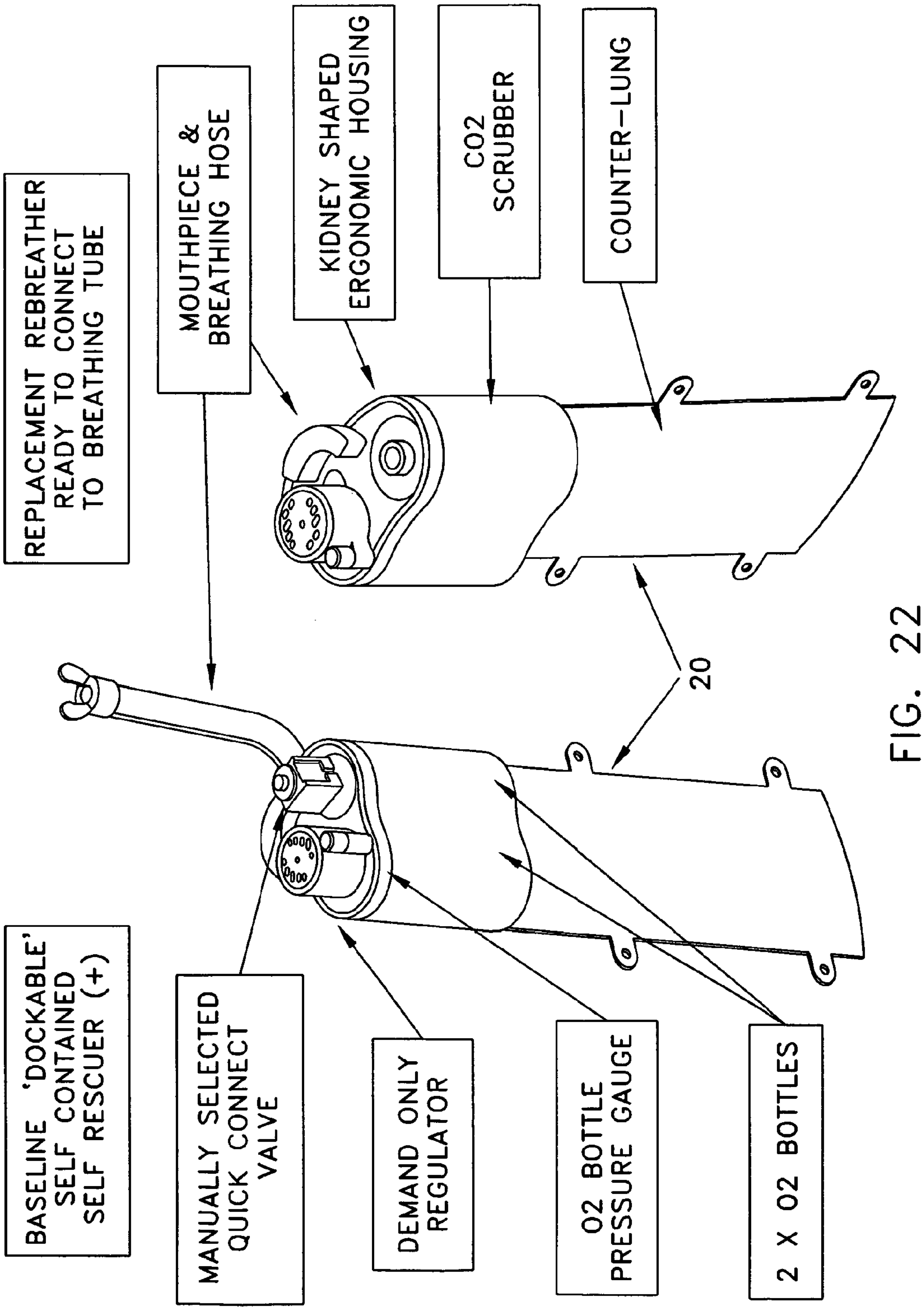

Looking next at FIGS. 18-21, it will be seen that quick disconnect 15 can be rotatably positioned in a variety of a configurations vis-à-vis breathing component 20 so as to provide a desired profile, e.g., so as to facilitate wearing on a belt, attachment to alternative breathing component, etc. Furthermore, breathing component 20 can have an ergonomic exterior shape so as to facilitate wearing it on a belt, e.g., the body of breathing component 20 can have a kidney-shaped cross-section and counterlung 35 can have a flat shape (when empty), etc. See, for example, FIG. 22.

Figure 23:
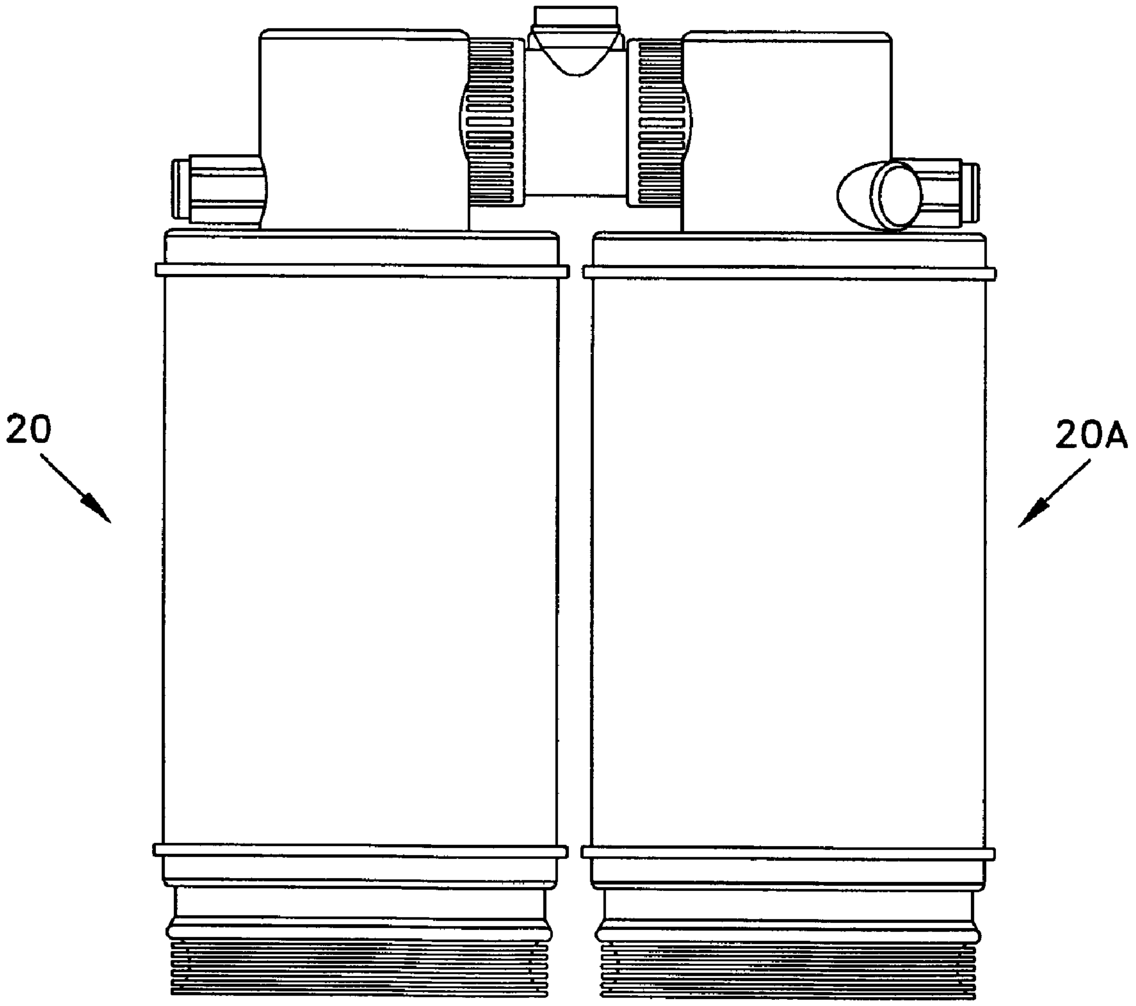
Figure 25:
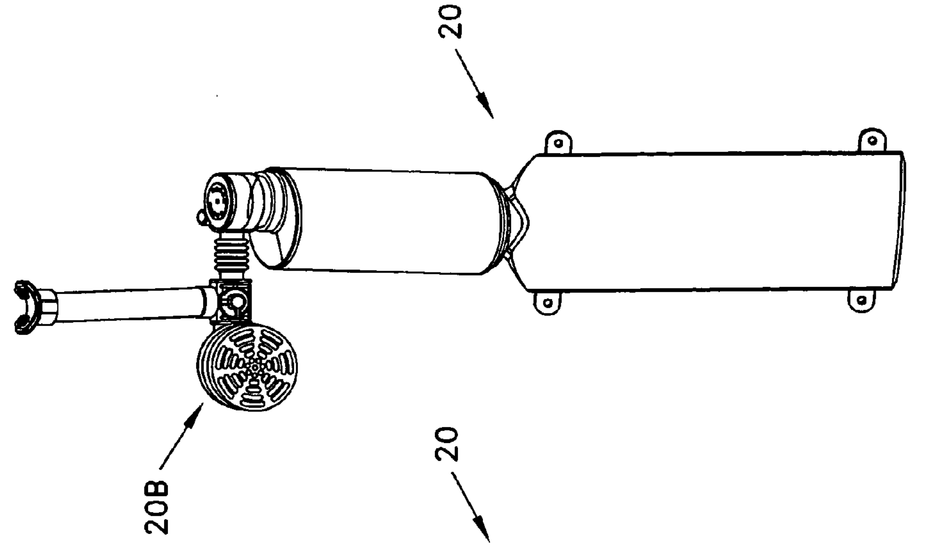
FIGS. 24-27 are schematic views illustrating various types of breathing components which can be connected to the safety quick disconnect.
Figure 26:
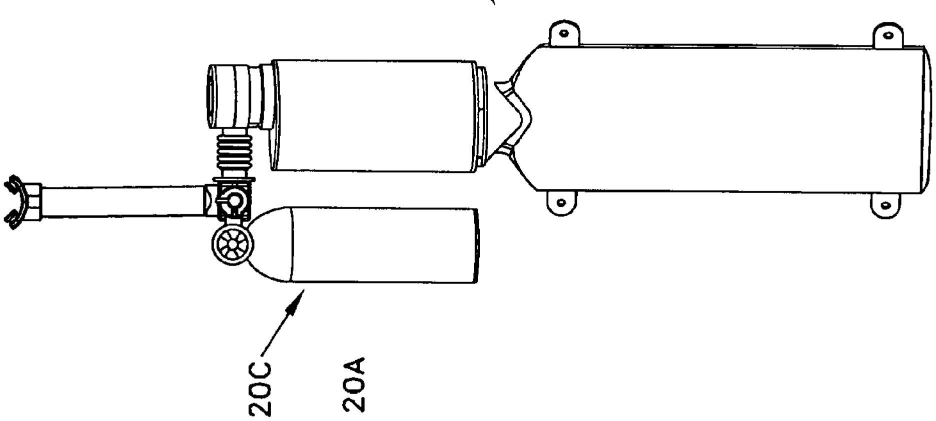
Figure 24:
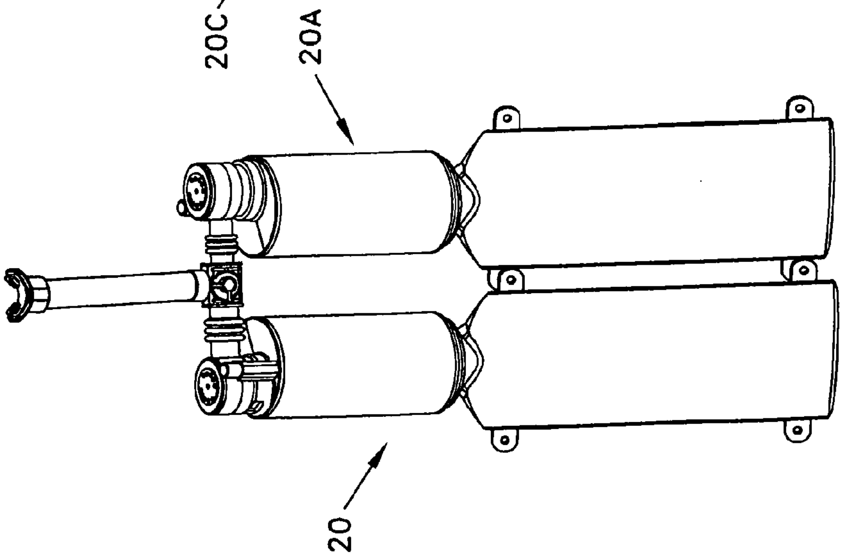
Figure 27:
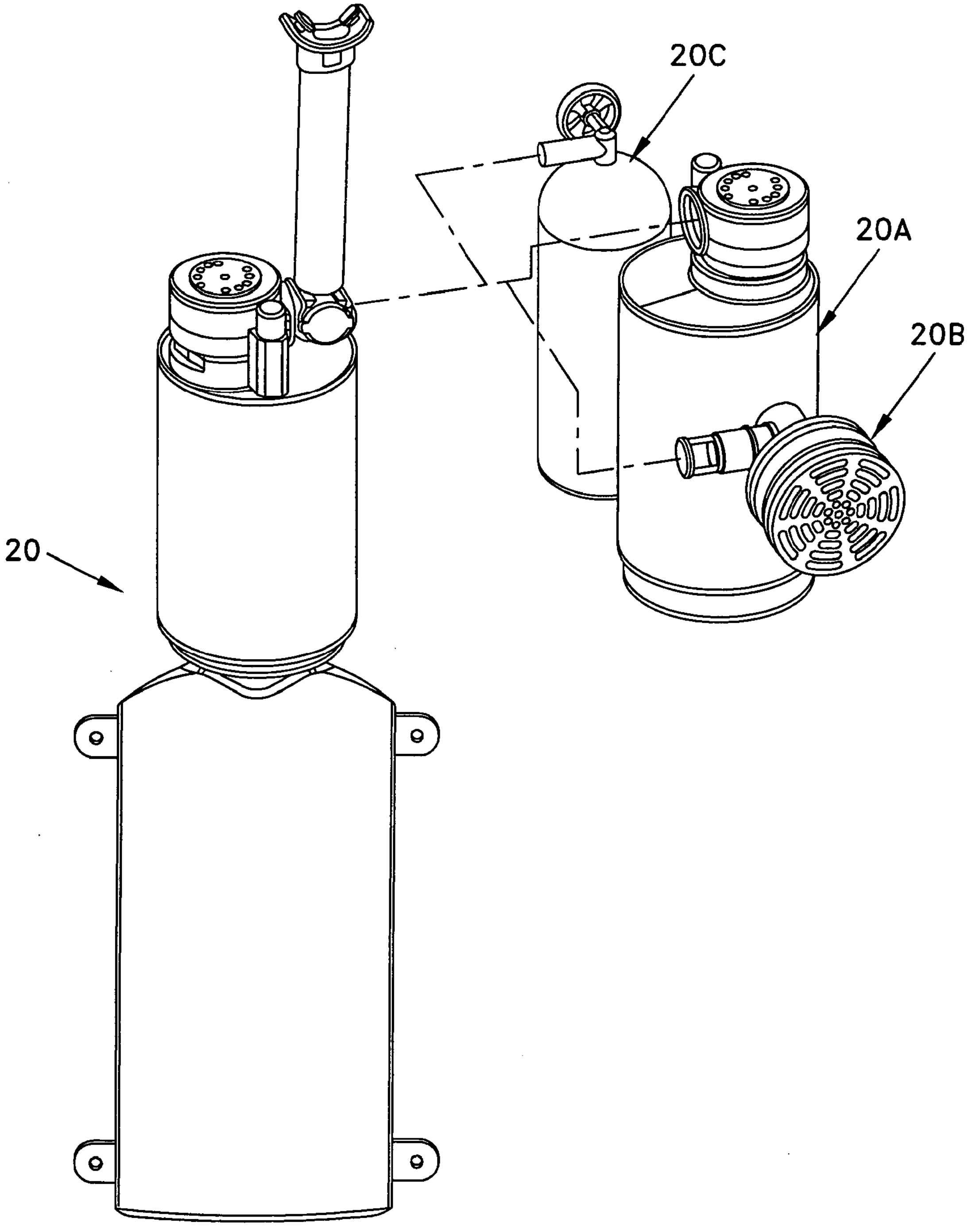

If desired, and as shown in FIGS. 23 and 24, quick disconnect 15 can be use to switch off between two identical breathing components 20, 20A. Alternatively, quick disconnect 15 can be connected to various other types of breathing components of the sort well known in the art, e.g., a carbon monoxide absorber 20B (FIG. 25), an oxygen bottle 20C (FIG. 26), etc. See also FIG. 27.

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A self-contained breathing apparatus (SCBA) comprising:
- a mouthpiece;
- a breathing component for providing breathable air, the breathing component comprising a component interface; and
- a safety quick disconnect comprising:
  - a valve body defining:
    - an internal chamber;
    - an opening communicating with the internal chamber and connectable with the mouthpiece;
    - first and second ports communicating with the internal chamber;
    - first and second mounts formed on the body adjacent to the first and second ports, respectively, for receiving the component interface of the breathing component, the first and second mounts being configured so as to place the breathing component into communication with the internal chamber when the component interface is in engagement with one or the other of the first and second mounts;
  - a valve spool selectively rotatably disposed within the internal chamber, wherein the valve spool comprises an L-shaped channel formed such that when the valve spool is appropriately rotated, the L-shaped channel (i) places the opening in communication with the first port, or (ii) places the opening in communication with the second port; and a lock mechanism for (i) preventing the valve spool from being rotated unless the component interface of the breathing component is positioned in one of the first and second mounts and a component interface of a replacement breathing component is positioned in the other of the first and second mounts, and (ii) preventing the removal of a component interface from a mount adjacent to a port which is in communication with the opening.

2. Apparatus according to claim 1 wherein the first and second mounts each comprise a U-shaped rail.

3. Apparatus according to claim 2 wherein the U-shaped rail comprises an overhang for capturing a component interface to the valve body.

4. Apparatus according to claim 1 wherein the lock mechanism comprises a pair of spring fingers mounted to the valve body for selective engagement in counterpart recesses formed in the valve spool.

5. Apparatus according to claim 4 wherein the valve body comprises four recesses.

6. Apparatus according to claim 1 wherein the lock mechanism is in a locked condition when a spring finger is engaged in a spool recess, and further wherein the lock mechanism is in a unlocked condition when no spring finger is engaged in a spool recess.

7. Apparatus according to claim 1 wherein the lock mechanism is constructed so that a given component interface cannot be withdrawn from one of the first and second mounts unless a different component interface is disposed in the other of the first and second mounts.

8. Apparatus according to claim 1 wherein the safety disconnect further comprises a valve knob for rotating the valve spool, and further wherein the lock mechanism comprises an peripheral extension on the valve knob for preventing the removal of a component interface from a mount adjacent to a port which is in communication with the opening.

9. Apparatus according to claim 1 wherein the breathing component comprises an air tank.

10. Apparatus according to claim 1 wherein the breathing component comprises a filter.

11. Apparatus according to claim 10 wherein the breathing component comprises a carbon monoxide absorber.

12. Apparatus according to claim 1 wherein the breathing component comprises the working portion of a self-contained breathing apparatus (SCBA).

13. Apparatus according to claim 12 wherein the working portion of the self-contained breathing apparatus (SCBA) comprises a carbon dioxide scrubber, and a counterlung.

14. Apparatus according to claim 13 wherein the counterlung is sized so as to have a volume which is approximately equal to the tidal volume of a pair of adult lungs.

15. Apparatus according to claim 13 wherein the working portion of the self-contained breathing apparatus (SCBA) further comprises a demand regulator disposed between the carbon dioxide scrubber and the component interface.

16. Apparatus according to claim 15 wherein the working portion of the self-contained breathing apparatus (SCBA) further comprises an oxygen supply connected to the demand regulator, and further wherein the demand regulator is configured to release oxygen from the oxygen supply when the pressure in the demand regulator falls below a given threshold.

* * * * *